United States Patent [19]
Chikaraishi et al.

[11] Patent Number: 6,096,779
[45] Date of Patent: Aug. 1, 2000

[54] AMORPHOUS PIRETANIDE, PIRETANIDE POLYMORPHS, PROCESS FOR THEIR PREPARATION AND THEIR USE

[75] Inventors: Yuji Chikaraishi, Saitama; Yoshihisa Matsuda, Kyoto; Makoto Otsuka, Osaka, all of Japan

[73] Assignee: Hoechst Pharmaceuticals & Chemicals K.K., Tokyo, Japan

[21] Appl. No.: 08/894,412

[22] PCT Filed: Feb. 12, 1996

[86] PCT No.: PCT/IB96/00254

§ 371 Date: Nov. 20, 1997

§ 102(e) Date: Nov. 20, 1997

[87] PCT Pub. No.: WO96/26197

PCT Pub. Date: Aug. 29, 1996

[30] Foreign Application Priority Data

Feb. 22, 1995 [JP] Japan ..................................... 7-033215
Feb. 22, 1995 [JP] Japan ..................................... 7-033216

[51] Int. Cl.[7] .......................... A61K 31/40; C07D 207/04; C07D 207/12; C07D 207/16

[52] U.S. Cl. ............................................ 514/429; 548/577

[58] Field of Search .............................. 514/429; 548/577

[56] References Cited

FOREIGN PATENT DOCUMENTS

| | | |
|---|---|---|
| 0 243 891 A2 | 11/1987 | European Pat. Off. . |
| 0 465 841 A2 | 1/1992 | European Pat. Off. . |
| 2 373 280 | 7/1978 | France . |
| 24 19 970 | 11/1975 | Germany . |
| 52-83547 | 7/1977 | Japan . |
| 5-230044 | 9/1993 | Japan . |

OTHER PUBLICATIONS

Y. Matsuda et al., "Amorphism and Physiochemical Stability of Spray–dried Frusemide", J. Pharm. Pharmacol., 44:627–633 (1992).

Y. Chikaraishi et al., "Preparation of Piretanide Polymorphs and Their Physicochemical Properties and Dissolution Behaviors", Chem. Pharm. Bull., 42(5):1123–1128 (1994).

CAS Online structure search; frusemide structures; pp. 5 and 6.

*Primary Examiner*—Joseph McKane
*Assistant Examiner*—Jane C. Osweeki
*Attorney, Agent, or Firm*—Finnegan, Henderson, Farabow, Garrett & Dunner, L.L.P.

[57] ABSTRACT

Amorphous piretanide having the following characteristics a) exothermic peaks at about 136° C. and about 209° C., b) an endothermic peak at about 207° C., and c) a melting peak at about 225° C. in differential thermal curves; d) a halo-pattern without diffraction peak in X-ray powder diffraction analysis; and e) characteristic absorptions at around 1700 $cm^{-1}$ and 3200–3500 $cm^{-1}$ in infra-red absorption spectrum, and having a superior solubility around neutrality and a high bioavailability effective in the manner of oral or injection administration. Methods of preparing amorphous piretanide are also described.

10 Claims, 9 Drawing Sheets

AMORPHOUS PIRETANIDE, PIRETANIDE POLYMORPHS, PROCESS FOR THEIR PREPARATION AND THEIR USE

This application is a 371 of PCT/IB96/00254 filed Feb. 12, 1996.

This invention relates to a novel amorphous piretanide, a novel class of piretanide polymorphs, a process for their preparation and their use.

Piretanide [chemical name: 4-phenoxy-3-(1-pyrrolidinyl)-5-sulfamoyl-benzoic acid] is known to be a pharmaceutical agent as a diuretic drug. The amorphous piretanide and the piretanide polymorph of this invention have a high solubility in an aqueous solution at various pH values and consequently can show a higher bioavailability.

A substance having the same chemical composition, but a different crystalline structure and a crystalline form, has been referred to as "polymorph". In general, it is known that many organic compounds have their polymorphs, depending upon differences in the sort of recrystallization solvents, pH values, temperatures and pressures in recrystallization.

Piretanide is usually recrystallized from a mixed solvent of methanol and water (hereinafter referred to as piretanide form A: See, Japanese Patent Kokai No.: 83547/1977). However, it has a water solubility as low as 7.9 mg/100 ml (at 20° C.) and, particularly, it is further slightly soluble in an acidic environment. For instance, piretanide form A has a solubility (at 37° C.) of 7.5 mg/100 ml and 4.2 mg/100 ml in a buffer at a pH value of 1 and 3, respectively.

For improving the slight solubility of piretanide form A in an acidic environment, there has been suggested a piretanide polymorph obtained by crystallizing piretanide from a lower aliphatic alcohol or a cyclic ether to form a crystalline solvate and then heating the resultant solvate (hereinafter referred to as piretanide form B: See, Japanese Patent Kokai No.: 230044/1993 and Chem. Pharm. Bull., (1994), Vol. 42, pp. 1123–1128). Piretanide form B has a solubility (at 37° C.) of 12.4 mg/ml and 6.4 mg/100 ml in a buffer at a pH value of 1 and 3, respectively, and its solubility in an acidic environment increased by a factor of 1.5–1.7 than that of piretanide form A. In view of a pH value of about 1 in gastric juice, piretanide form B has a crystalline form more suitable for oral administration.

Piretanide has been applied n to only as a pharmaceutical preparation for oral administration but also an injection and, in the latter case, its higher solubility at a pH value around neutrality is desirable. As piretanide forms A and B have a solubility of 193.8 mg/100 ml and 195.4 mg/100 ml at a pH value of 6.8 (at 37° C.), respectively, they have a higher solubility than that in an acidic environment. Nevertheless, there has been desired a crystalline piretanide having a far higher solubility at a pH value around neutrality.

It is therefore a primary object of this invention to provide a crystalline piretanide having an excellent solubility at a pH value around neutrality.

According to this invention, there is provided 1) an amorphous piretanide having the following characteristics:
    (a) exothermic peaks at about 136° C. and about 209° C.,
    (b) an endothermic peak at about 207° C., and
    (c) a melting peak at about 225° C. in differential thermal curves;
    (d) a halopattern without diffraction peak (2θ) in X-ray powder diffraction analysis; and
    (e) characteristic absorptions at around 1700 cm$^{-1}$ and 3200–3500 cm$^{-1}$ in an infra-red absorption spectrum; and 2) a piretanide polymorph having the following characteristics:
    (a) an endothermic peak at about 132° C.,
    (b) an exothermic peak at about 143° C., and
    (c) a melting peak at about 224° C., in differential thermal curves;
    (d) diffraction peaks (2θ) at 10.5, 12.2, 15.6, 19.1, 19.9, 22.0, 22.8, 25.6 and 30.6° in X-ray powder diffraction analysis, and
    (e) characteristic absorptions at around 1700 cm$^{-1}$ and 3200–3500 cm$^{-1}$ in an infra-red absorption spectrum.

According to this invention, there is also provided a process for preparing 1) the above-defined amorphous piretanide which comprises dissolving piretanide in an aqueous solution of a base, adjusting a pH value of the solution by an acid to a pH range from not less than 3.87 to not more than 4.37 and recovering the precipitate thus separated;

2) the above-defined piretanide polymorph which comprises dissolving piretanide in an aqueous solution of a base, adjusting a pH value of the solution to a pH range of less than 3.50 by an acid and recovering the precipitate thus separated.

Moreover, there is also provided a method for the treatment and prevention of edema having administering an effective amount of the above-mentioned amorphous piretanide or piretanide polymorph and a pharmaceutically acceptable carrier.

Figure 1:
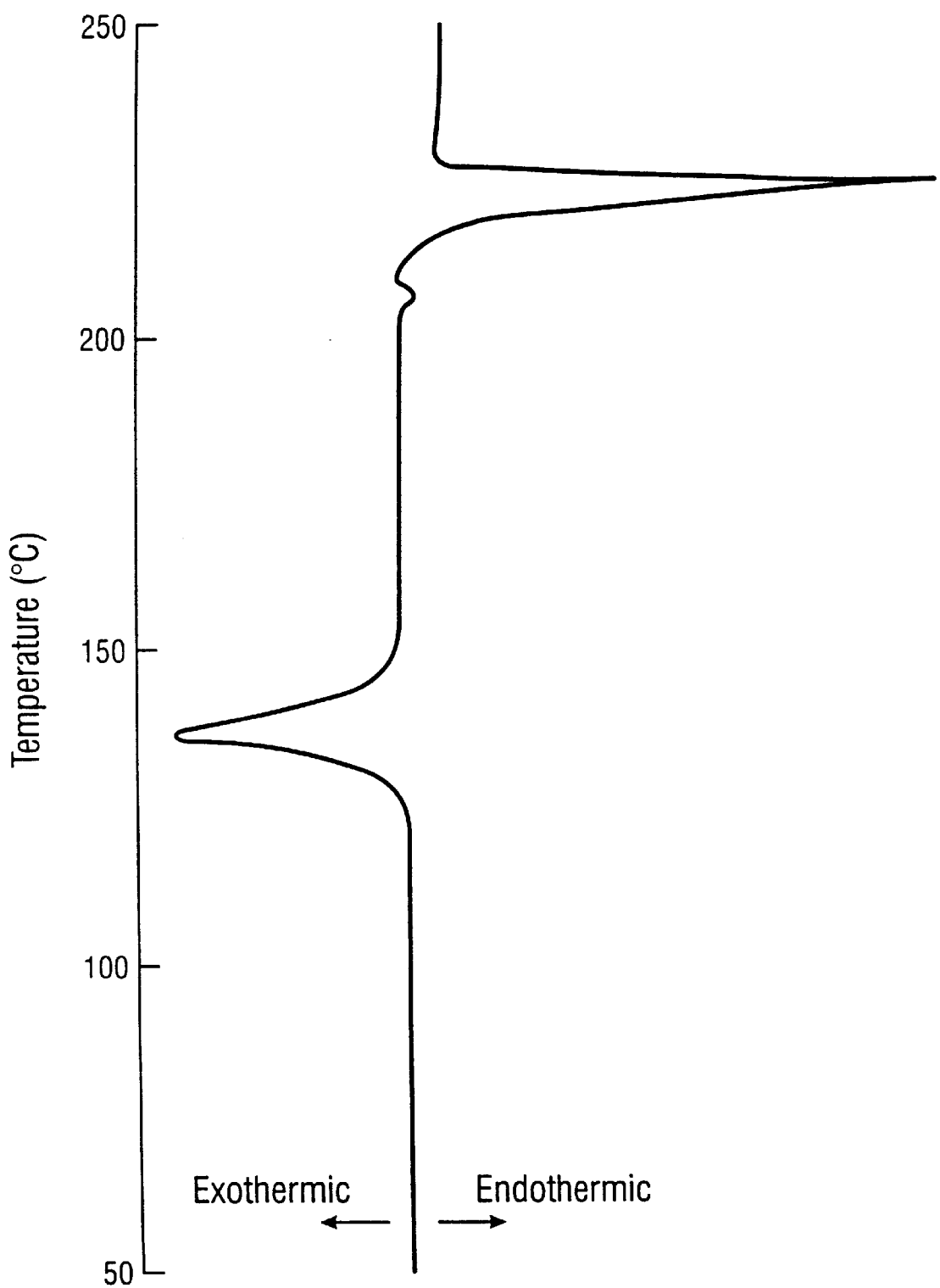
FIG. 1 shows a differential thermal curve of the present amorphous piretanide.

It is apparent that the present piretanide crystals (according to FIG. 4) are amorphous, since no diffraction peak which indicates to be crystalline appears in X-ray powder diffraction analysis. The present amorphous piretanide shows, as stated above, characteristic peaks different from those of the piretanide crystals previously known in the differential thermal curves, X-ray powder diffraction analysis and infra-red absorption spectrum.

According to the present process for preparing an amorphous piretanide, piretanide is first dissolved in an aqueous solution of a base at room temperature with stirring. The solvent which is employed in this invention includes water and an aqueous organic solvent such as aqueous alcohol, e.g. aqueous methanol, aqueous ethanol, aqueous propanol and the like. The aqueous solution of a base includes, for example, those aqueous solutions of bases such as sodium hydroxide, potassium hydroxide, sodium carbonate and the like. A basic aqueous solution of piretanide has a pH value of 11–13, preferably a pH value of 12. To the basic aqueous solution of piretanide is then added an aqueous solution of an acid to adjust a pH value of the resulting solution to a range from not less than 3.87 to not more than 4.37, preferably a pH value of 4.0–4.3.

The pH value to be adjusted herein is significant and a pure amorphous piretanide can be obtained within the pH range as defined above. In a pH range of less than 3.87 and more than 3.50, there is obtained a mixture of amorphous piretanide and piretanide polymorph having a different crystalline form from said piretanide and then it is undesirably required to carry out an additional separating procedure of the crystals of two forms. At a pH range of less than 3.50, there is obtained the pure piretanide polymorph as stated above, while the precipitates cannot be satisfactorily separated out at a pH range of more than 4.37.

The aqueous solution of an acid which is employed in this invention includes a aqueous solution of inorganic or organic acids such as hydrochloric acid, sulfuric acid, phosphoric acid or acetic acid, and an aqueous solution of hydrochloric acid is particularly preferable.

The precipitates thus separated out (the present amorphous piretanide) are then recovered by filtration and dried in the presence of a drying agent such as phosphorus pentoxide and the like under reduced pressure, preferably 15 mmHg or lower, at room temperature for a period of 10 or more hours, preferably for a period of 12–15 hours.

The present amorphous piretanide is confirmed to be one of the piretanide polymorphs according to HPLC and TLC and then the physico-chemical properties thereof, as well as solubility in an aqueous solution of various pH values are investigated.

Differences in properties between the present amorphous piretanide and piretanide form A will be discussed hereinbelow from the standpoint of physico-chemical properties, using thermal analysis (differential thermal curve), X-ray powder diffraction analysis and infra-red absorption spectrum.

Figure 3:
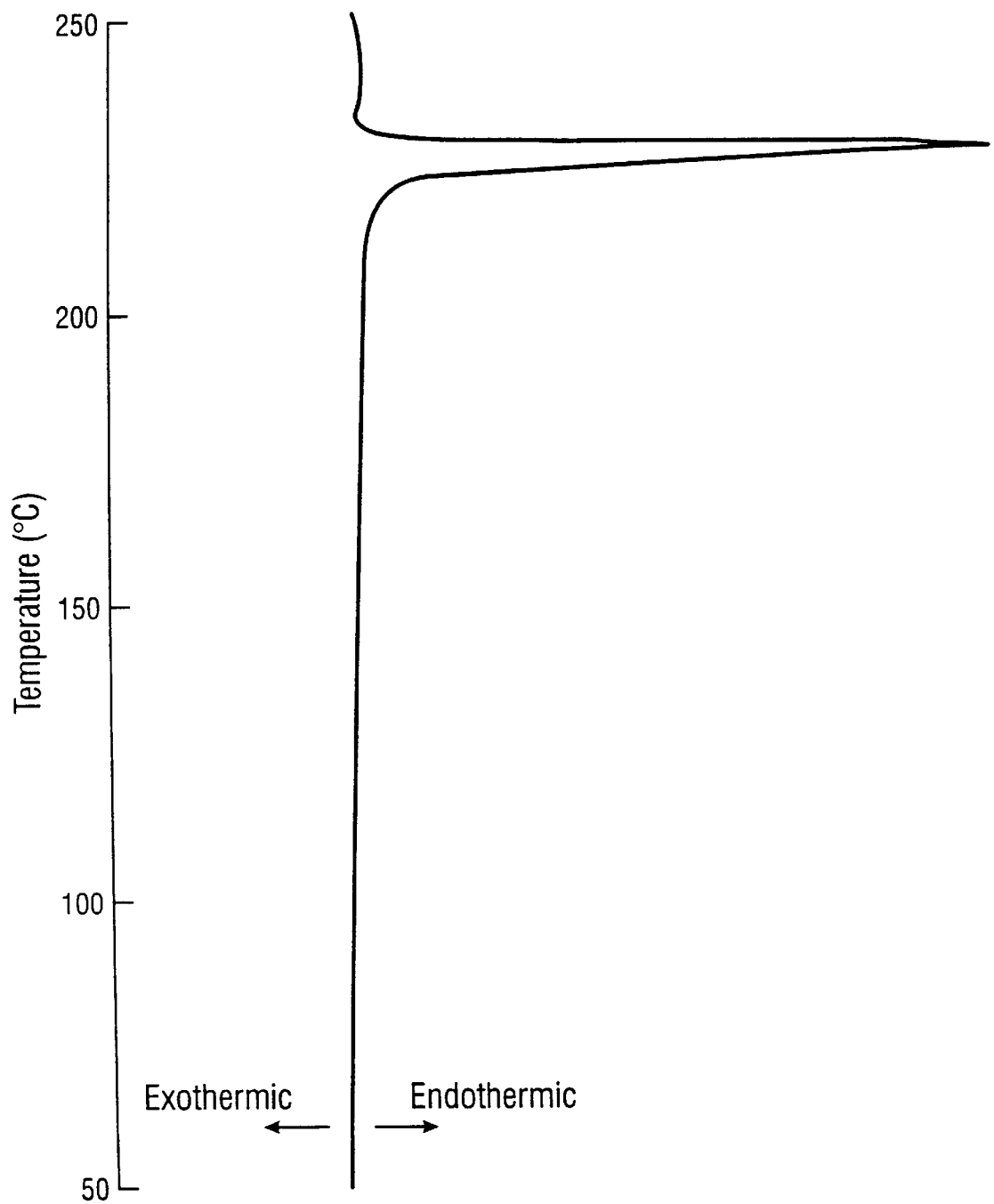
FIG. 3 shows a differential thermal curve of piretanide form A.
Figure 4:
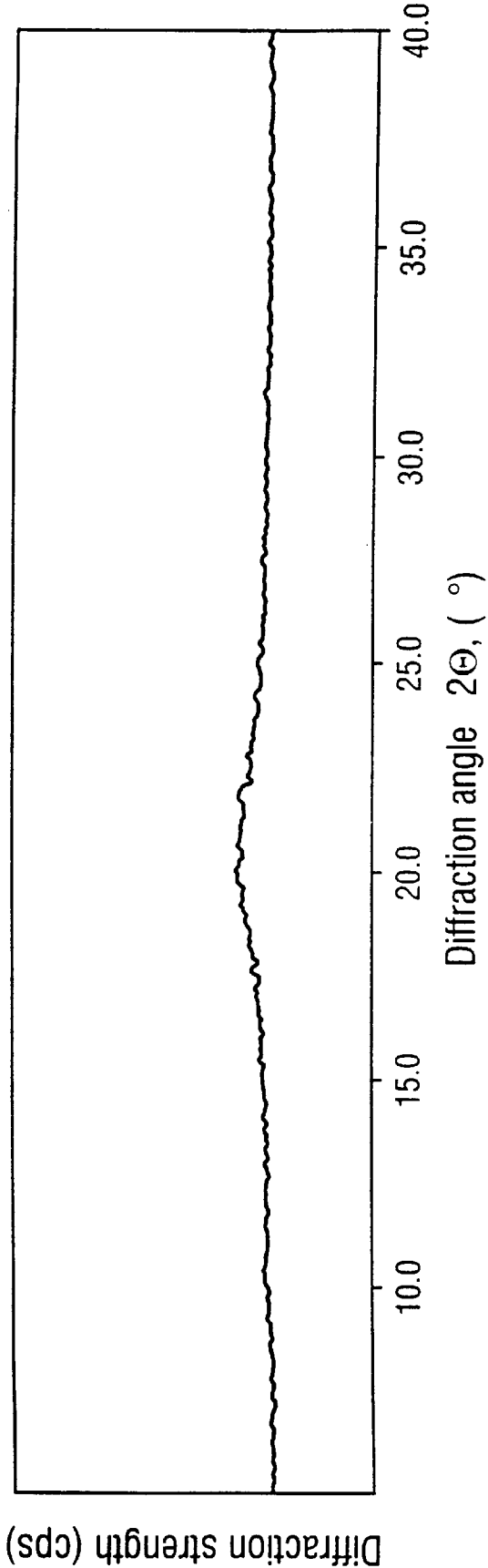
FIG. 4 shows an X-ray powder diffraction pattern of the present amorphous piretanide.
Figure 6:
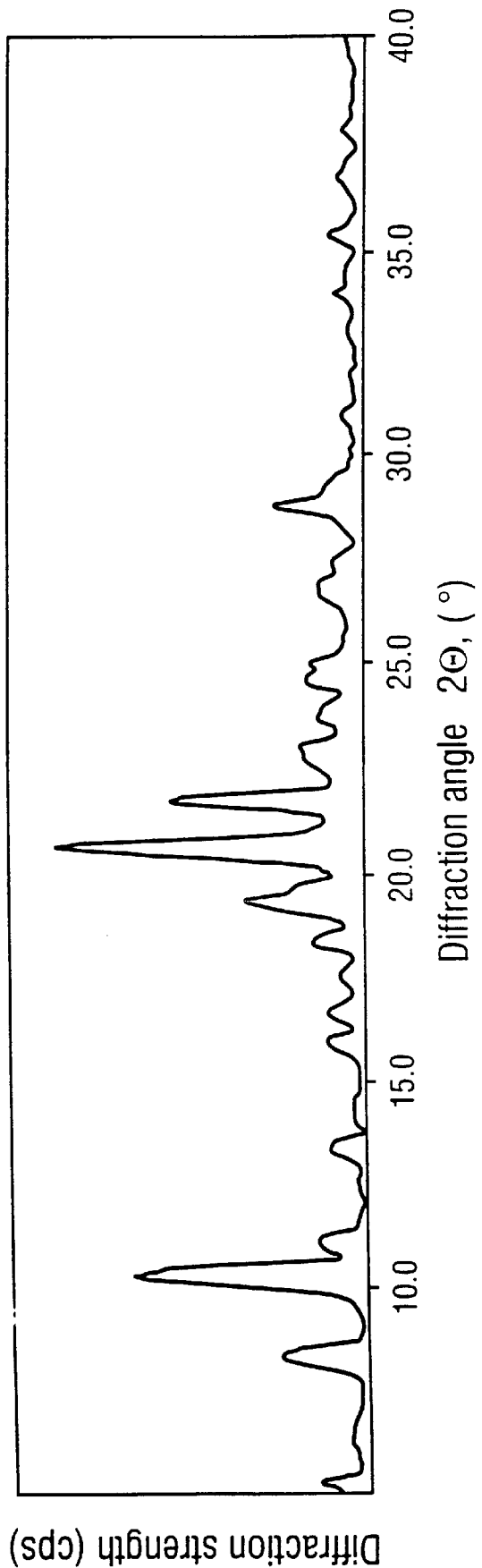
FIG. 6 shows an X-ray powder diffraction pattern of piretanide form A.
Figure 7:
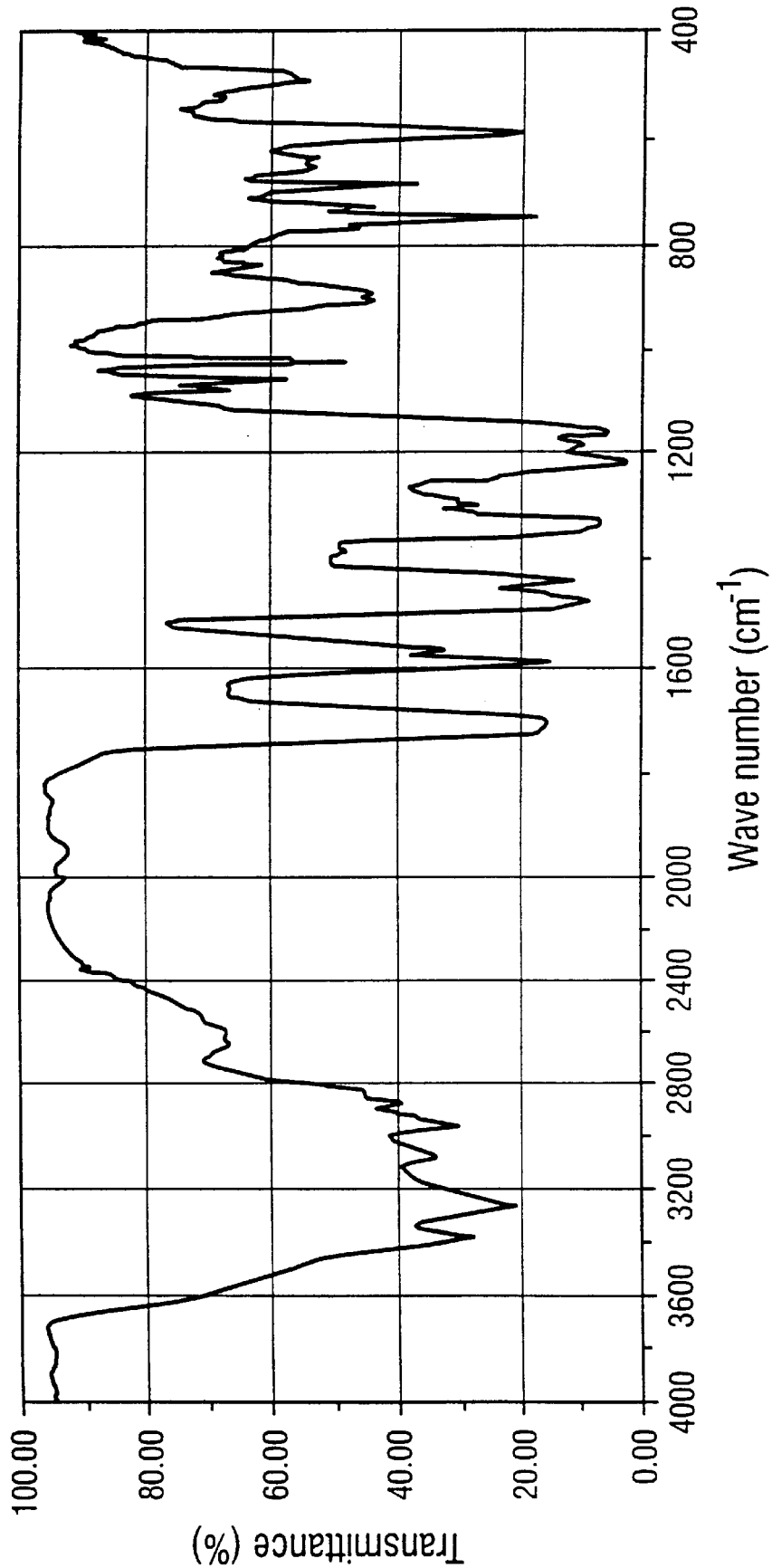
FIG. 7 shows an infra-red absorption spectrum of the present amorphous piretanide.
Figure 9:
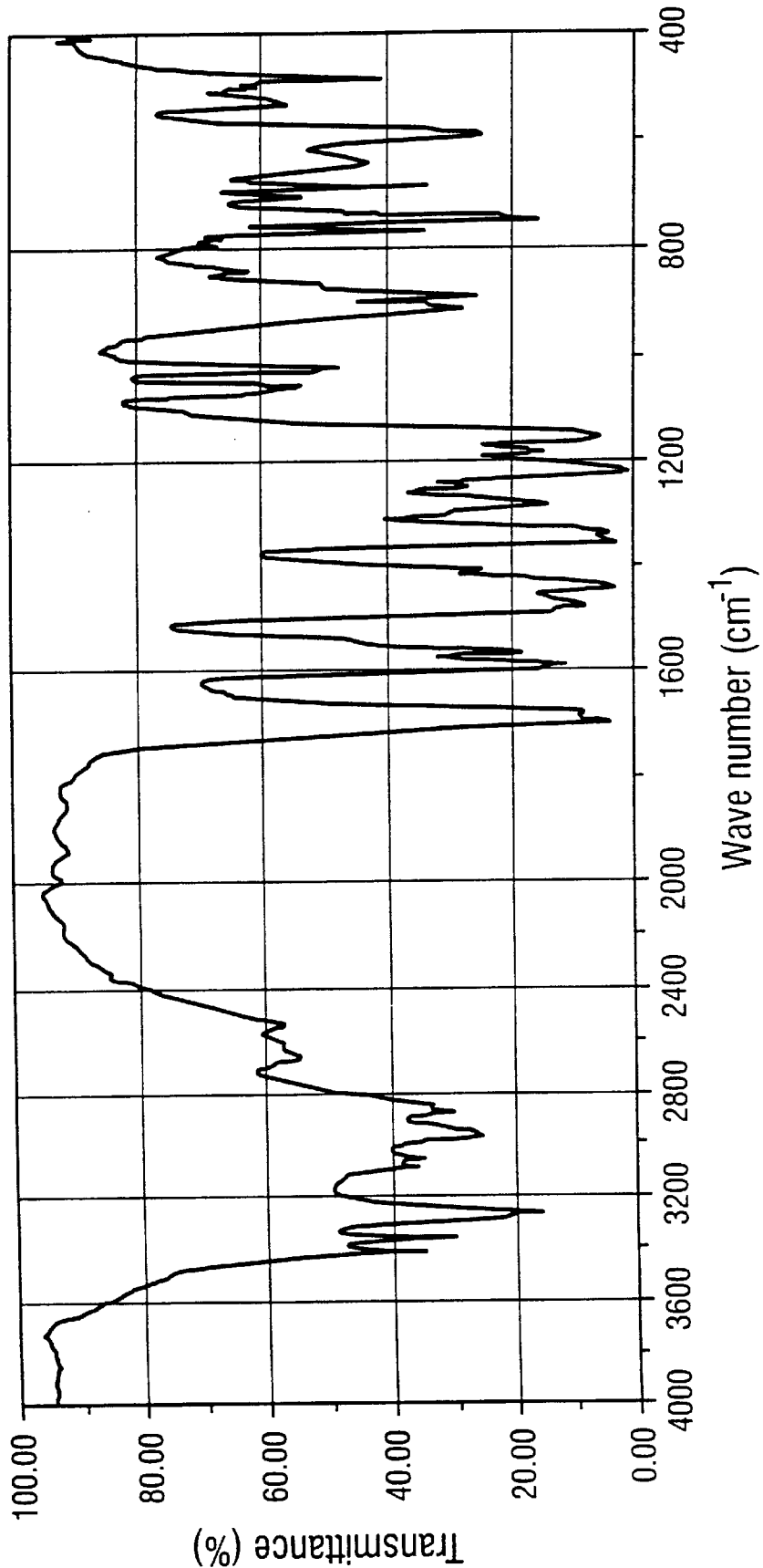
FIG. 9 shows an infra-red absorption spectrum of piretanide form A.

The present amorphous piretanide shows a melting peak at about 225° C. after showing an exothermic peak at about 136° C. due to a change in crystalline forms and continuous peaks of endothermic at about 207° C. and exothermic at about 209° C. due to a melting re-crystallization in the differential thermal curves as seen in FIG. 1, which is clearly different from piretanide form A as seen in FIG. 3. In the X-ray powder diffraction, all the peaks including characteristic peaks of piretanide form A (2θ=8.3, 10.3, 13.2, 20.7 and 21.7°) disappear and a halo-pattern (See, J. Pharm. Pharmacol., 1992, Vol. 44, pp. 627–633) is seen. The results of the X-ray powder diffraction analysis of the present amorphous piretanide and piretanide form A are shown in FIGS. 4 and 6, respectively. The infra-red absorption spectrum exhibits that two peaks around 1700 cm$^{-1}$ attributable to a stretching vibration in carboxylic acid of piretanide form A were shifted to a somewhat higher wave number side to form one peak, while the two peaks of piretanide form A at 3359 cm$^{-1}$ attributable to a stretching vibration in sulfonamide and 3411 cm$^{-1}$ attributable to a stretching vibration in carboxylic acid have an absorption spectrum which forms one peak with a shoulder curve at 3386 cm$^{-1}$. The infra-red absorption spectra of the present amorphous piretanide and piretanide form A are shown in FIGS. 7 and 9, respectively.

The present amorphous piretanide has been confirmed to contain one molecule of water per two molecules of piretanide according to moisture determination, whereas piretanide form A does hardly contain water. In regard to solubility in an aqueous solution at various pH values, the present piretanide in an acidic environment showed a solubility of 15.2 mg/100 ml and 6.5 mg/100 ml in a buffer at a pH value of 1 and 3, which increased by a factor of 2.0 and 1.5 than those of piretanide form A, respectively. In addition, the amorphous piretanide in a neutral environment showed a solubility of 901.3 mg/100 ml in a buffer at a pH value of 6.8, which increased by a factor of 4.5 than that of piretanide form A.

The present piretanide polymorph shows, as stated above, characteristic peaks different from those of the piretanide crystals previously known in the differential thermal curves, X-ray powder diffraction analysis and infra-red absorption spectrum (see FIGS. 2, 3, 5, 6, 8, 9).

According to the present process for preparing a piretanide polymorph, piretanide is first dissolved in an aqueous solution of a base at room temperature with stirring. The solvent which is employed in this invention includes water and an aqueous organic solvent such as aqueous alcohol, e.g. aqueous methanol, aqueous ethanol, aqueous propanol and the like. The aqueous solution of a base includes, for example, those aqueous solutions of bases such as sodium hydroxide, potassium hydroxide, sodium carbonate and the like. A basic aqueous solution of piretanide has a pH value of 11–13, preferably a pH value of 12.

To the basic aqueous solution of piretanide is then added an aqueous solution of an acid to adjust a pH value of the resulting solution to a range of less than 3.50, preferably a pH value of 2.0–3.4. The pH value to be adjusted herein is significant and a pure piretanide polymorph can be obtained within the pH range as defined above. In a pH range of not less than 3.50 to not more than 3.87, there is obtained a mixture of the present piretanide polymorph and another different amorphous piretanide and then it is undesirably required to perform an additional separating procedure of the crystals of two forms. At a pH range of not less than 3.87, there is obtained the pure amorphous piretanide as stated above.

The aqueous solution of an acid which is employed in this invention includes an aqueous solution of inorganic or organic acids such as hydrochloric acid, sulfuric acid, phosphoric acid or acetic acid, and an aqueous solution of hydrochloric acid is particularly preferable. The precipitates thus separated out (the present piretanide polymorph) are then recovered by filtration and dried in the presence of a drying agent such as phosphorus pentoxide and the like under reduced pressure, preferably 15 mmHg or lower, at room temperature for a period of 10 or more hours, preferably for a period of 12–15 hours.

The present piretanide polymorph is confirmed to be one of the piretanide polymorphs according to HPLC and TLC and then the physico-chemical properties thereof, as well as solubility in an aqueous solution of various pH values are investigated.

Figure 2:
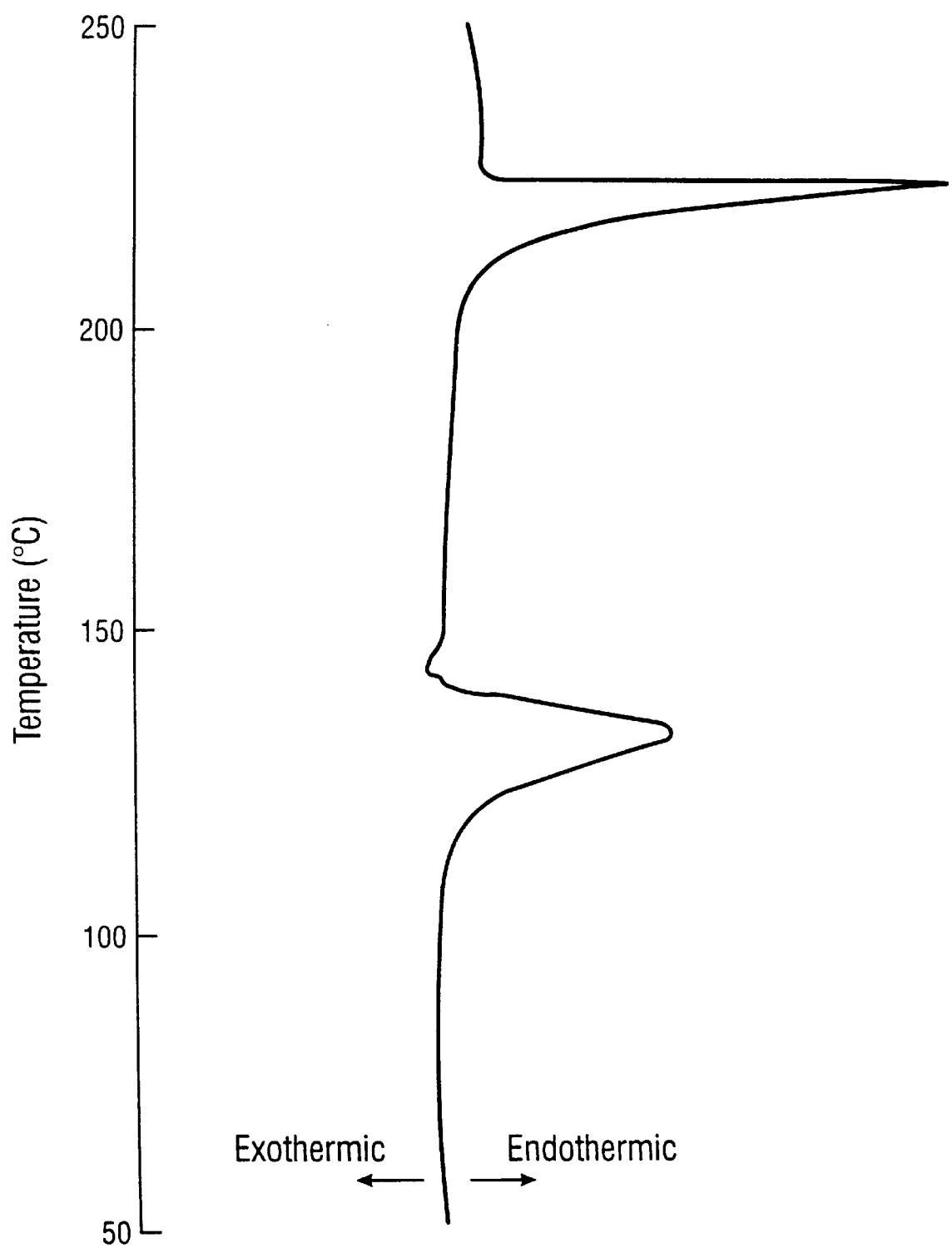
FIG. 2 shows a differential thermal curve of the present piretanide polymorph.
Figure 5:
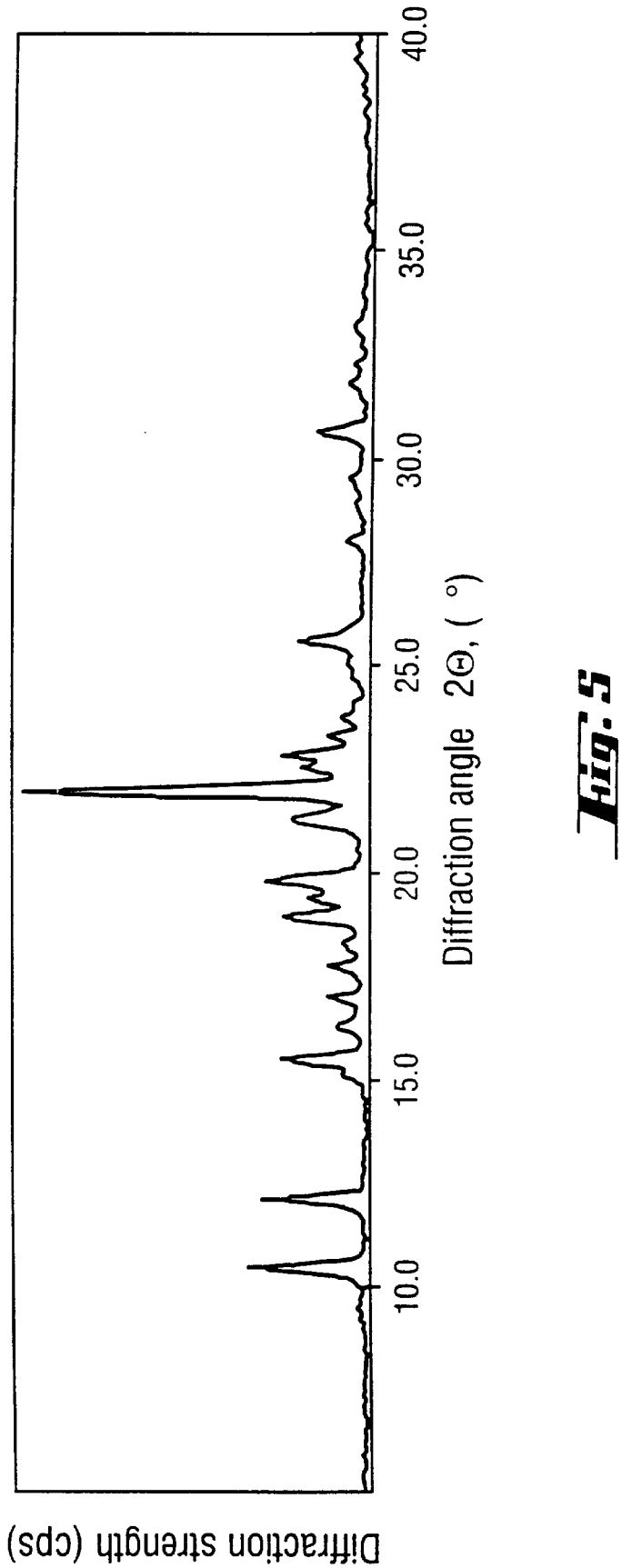
FIG. 5 shows an X-ray powder diffraction pattern of the present piretanide polymorph.
Figure 8:
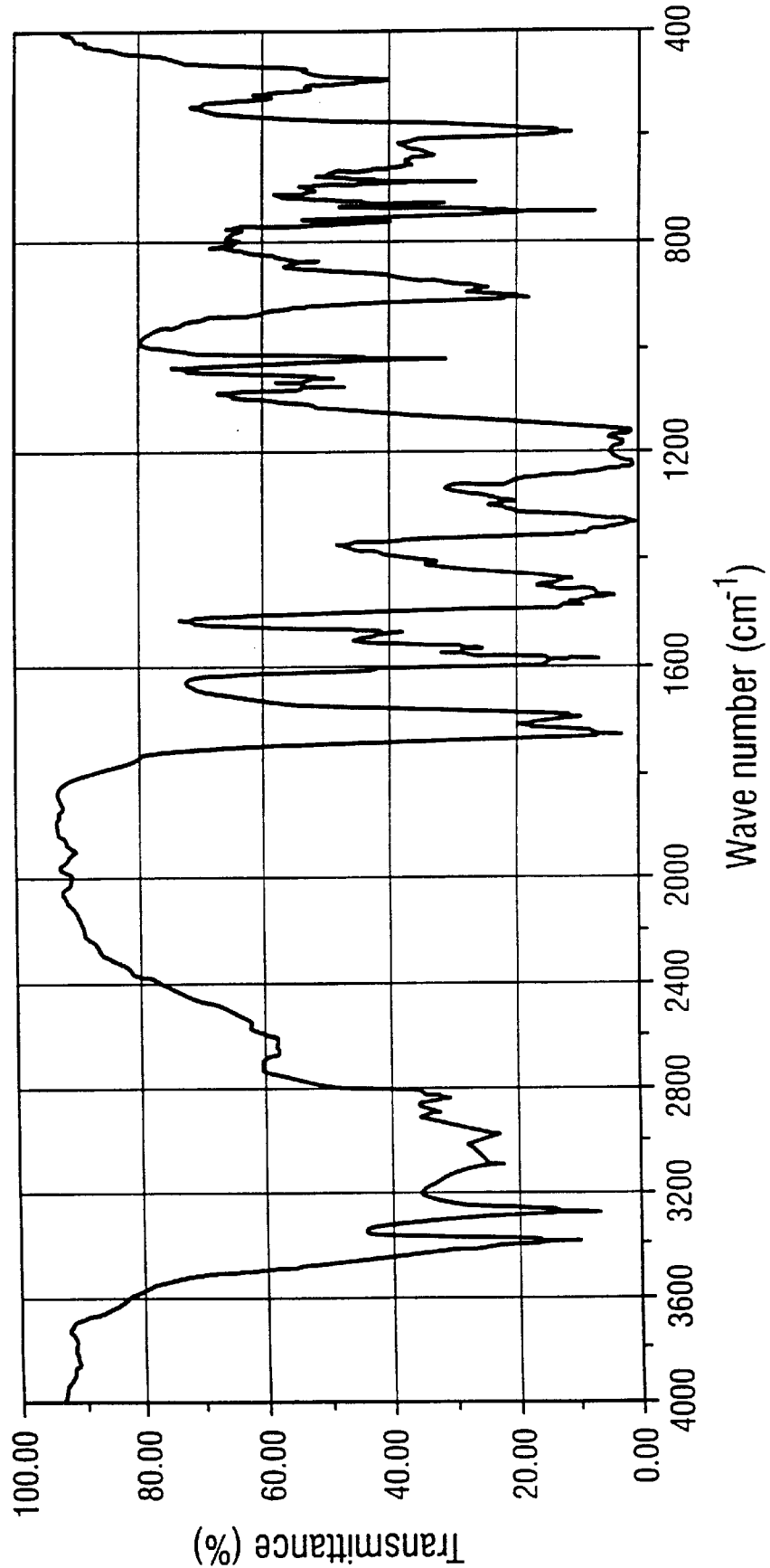
FIG. 8 shows an infra-red absorption spectrum of the present piretanide polymorph.

Differences in properties between the present piretanide polymorph and piretanide form A will be discussed hereinbelow from the standpoint of physico chemical properties, using thermal analysis (differential thermal curve), X-ray powder diffraction analysis and infra-red absorption spectrum. The present piretanide polymorph shows, in the differential thermal curves, continuous peaks of endothermic at about 132° C. and exothermic at about 143° C. and a melting peak at about 224° C. as seen in FIG. 2, which is clearly different from piretanide form A as seen in FIG. 3. In the X-ray powder diffraction, a part of characteristic peaks of piretanide form A (2θ=8.3, 10.3, 13.2, 20.7 and 21.7°) disappears and newly appear peaks (2θ=10.5, 12.2, 15.6, 19.1, 19.9, 22.0, 22.8, 25.6 and 30.6°). The results of the X-ray powder diffraction analysis of the present piretanide polymorph and piretanide form A are shown in FIGS. 5 and 6, respectively. The infra-red absorption spectrum exhibits that two peaks around 1700 cm$^{-1}$ attributable to a stretching vibration in carboxylic acid of piretanide form A were shifted to a higher wave number side, while the two peaks of piretanide form A at 3359 cm$^{-1}$ attributable to a stretching vibration in sulfonamide and 3411 cm$^{-1}$ attributable to a stretching vibration in carboxylic acid have an absorption spectrum which forms one peak with a shoulder curve at 3386 cm$^{-1}$. The infra-red absorption spectra of the present piretanide polymorph and piretanide form A are shown in FIGS. 8 and 9, respectively.

The present piretanide polymorph as obtained by the process described above is confirmed to contain one molecule of water per two molecules of piretanide according to moisture determination, whereas piretanide form A does hardly contain water.

In regard to solubility in an aqueous solution at various pH values, the present piretanide polymorph in an acidic environment showed solubilities of 12.2 mg/100 ml and 6.7 mg/100 ml in a buffer at a pH value of 1 and 3, respectively, all of which increased by a factor of 1.6 than those of piretanide form A. In addition, the present piretanide polymorph in a neutral environment showed a solubility of 927.3 mg/100 ml in a buffer at a pH value of 6.8, which increased by a factor of 4.8 than that of piretanide form A.

The invention also relates to pharmaceutical preparations comprising a compound of amorphous piretanide or piretanide polymorph.

Pharmaceutical preparations contain an effective amount of the active amorphous piretanide or piretanide polymorph and if necessary other active compounds together with an inorganic or organic pharmaceutically utilizable excipient. Administration can be carried out intranasally, intravenously, subcutaneously or orally. The dosage of the active compound depends on the mammalian species, the body weight, the age and the manner of administration.

The pharmaceutical preparations of the present invention are prepared in a dissolving, mixing, granulating or coating process known per se.

For a form for oral administration, the active compounds are mixed with the additives customary therefor such as excipients, stabilizers or inert diluents and brought by means of customary methods into suitable administration forms such as tablets, coated tablets, hard gelatin capsules, aqueous alcoholic or oily suspensions or aqueous, alcoholic or oily solutions. Inert excipients which can be used are, for example, gum arabic, magnesia, magnesium carbonate, potassium phosphate, lactose, glucose, magnesium stearyl fumarate or starch, in particular maize starch. The preparation in this case can be dry and moist granules. Suitable oily excipients or solvents are, for example, vegetable or animal oils, such as sunflower oil and cod liver oil.

For subcutaneous or intravenous administration, the active compounds or their physiologically tolerable salts are brought into solutions, suspensions or emulsions, if appropriate with the substances customary therefor such as solubilizers, emulsifiers or other auxiliaries. Suitable solvents are, for example, water, physiological saline solution or alcohols, such as ethanol, propanediol or glycerol, and sugar solutions such as glucose or mannitol solutions or mixtures of said solvents.

This invention will be more fully illustrated by way of the following examples, but they are not intended to limit the scope of this invention.

EXAMPLE 1

Preparation of Amorphous Piretanide

To 10 g of piretanide form A was added 1000 ml of 0.1 N sodium hydroxide and dissolved at room temperature. To the resulting solution was added 160 ml of 0.5 N hydrochloric acid with stirring at 700 rpm. After one of the precipitates once separated out was redissolved, 35 ml of 0.5 N hydrochloric acid was further added to adjust a pH value to 4.0, and the amorphous form thus separated out was recovered by filtration and then dried over phosphorus pentoxide under reduced pressure at room temperature for a period of 12 hours to obtain 9.2 g of the desired product.

EXAMPLE 2

Confirmation of Piretanide Polymorph

1) Confirmation of piretanide by HPLC

The amorphous form obtained as described in Example 1 was analyzed by HPLC in order to confirm that it is piretanide, as set forth below.

About 15 mg of the amorphous form was weighed and dissolved in 0.5 ml of a 0.1 N aqueous solution of sodium hydroxide and then water was added to make up to an exact volume of 10 ml. An aliquot of 2 ml of this solution was taken and made up to an exact volume of 25 ml with methanol, and used this solution as a sample solution. Performed was the test with 15 μl of a sample under the following conditions:

[Operation conditions]

Detector: an ultraviolet absorption photometer (wavelength: 254 nm)

Column: a stainless steel column 4 mm in inside diameter and 30 cm in length, packed with octadecylsilylated silica gel (10 μm in particle diameter) (μBondapak C18)

Mobile phase: a mixture of methanol, water and glacial acetic acid (60:40:0.2)

Consequently, the amorphous form obtained as described in Example 1 showed peaks at the same retention time as piretanide did.

2) Confirmation of piretanide by TLC

The amorphous form obtained as described in Example 1 was analyzed by TLC in order to confirm that it is piretanide.

About 10 mg of the amorphous form was weighed and dissolved in 1 ml of methanol, and used this solution as a sample solution. 10 μl of the test solution was spotted on a thin layer plate and developed with a developing solvent to a distance of about 10 cm and then the thin layer plate was air dried. The plate was irradiated with ultraviolet light (254 nm) and then observed.

[Operation conditions]

Thin layer plate: Silica gel 60F254 precoated plate with a thickness of 0.25 mm (available from E. Merck AG)

Developing solvent: a mixture of isopropanol, benzene and glacial acetic acid (14:6:1), a mixture of chloroform, methyl ethyl ketone and glacial acetic acid (50:50:1), a mixture of isopropanol, methyl ethyl ketone and glacial acetic acid (50:50:1.)

Consequently, the amorphous form obtained as described in Example 1 showed the same $R_f$ value as piretanide did in the three developing solvents as defined above.

EXAMPLE 3

Instrumental Analysis of Piretanide (Differential Thermal Curve, X-ray Powder Diffraction and Infra-red Absorption Spectrum)

The amorphous form obtained as described in Example 1 was analyzed with differential thermal curve (Rigaku Denki K.K., Type: 8085E2), X-ray powder diffraction (Mac Science K.K., Type: MXP$^3$) and infra-red absorption spectrum (JEOL Co., Type: JIR5500), using piretanide form A as a control. The results are shown in FIGS. 1, 3, 4, 6, 7, 9.

EXAMPLE 4

Moisture Determination of Amorphous Piretanide

The moisture content of about 10 mg of the amorphous piretanide obtained as described in Example 1 was determined by means of a moisture determination apparatus (Hiranuma Sangyo K.K., Type: AQ 5).

Consequently, the moisture content as determined by the apparatus was about 0.22 mg. On the basis of the molecular weight of piretanide (367.40) and the molecular weight of water (18.0), it has been found that one molecule of water is included per two molecules of piretanide.

EXAMPLE 5

Solubility of Amorphous Piretanide

The amorphous piretanide obtained as described in Example 1 was analyzed for solubility in a buffer at various pH values by means of a dissolution tester, using piretanide form A as a control.

A sufficient amount of the amorphous piretanide to ensure supersaturation was added to 500 ml each of the buffers at various pH values as indicated below, and about 10 ml of a solution was sampled at appropriate intervals and filtered using a 0.45 μm filter. About 5 ml of the initial solution was discarded and the remainder was used as a sample solution and, if required, diluted with the same buffer. Solubility was determined by absorbance at 275 nm.

[Operation conditions]

Buffer: pH 1 Potassium chloride-hydrochloric acid system pH 3 Sodium chloride-glycine-hydrochloric acid system pH 6.8 JP XII, second fluid Solution temperature: 37° C.

Solvent volume: 500 ml

Rotating speed: 200 rpm

Consequently, the amorphous piretanide showed a solubility of 15.2 mg and 6.5 mg in 100 ml each of the buffers at a pH value of 1 and 3, respectively, and the respective solubility increased by a factor of 2.0 and 1.5 than that of piretanide form A (7.5 mg/100 ml at a pH value of 1 and 4.2 mg/100 ml at a pH value of 3). The amorphous piretanide in a neutral environment showed a solubility of 901.3 mg in 100 ml of a buffer at a pH value of 6.8 and its solubility increased by a factor of 4.7 than that of piretanide form A (193.8 mg/100 mg).

As apparent from the above results, the present amorphous piretanide can show a superior solubility in an aqueous solution in acidic and neutral environments, especially in a neutral envinronment. For instance, the solubility at 37° C. in a buffer at a pH value of 1 of the present amorphous piretanide increased by a factor of 2 and 1.2 than that of piretanide forms A and B, respectively, while its solubility increased by a factor of 4.7 and 4.6 at 37° C. in a buffer at a pH value of 6.8 than those of piretanide forms A and B, respectively. As gastric juice has a pH value of about 1 and an injection has been usually adjusted to a neutral state, the present amorphous piretanide has a higher bioavailability and can be preferably used for a pharmaceutical preparation for oral administration and an injection.

EXAMPLE 6

Preparation of Piretanide Polymorph

To 10 g of, piretanide form A was added 1000 ml of 0.1 N sodium hydroxide and dissolved at room temperature. To the resulting solution was added 160 ml of 0.5 N hydrochloric acid with stirring at 700 rpm. After an precipitates once separated out was redissolved, 0.5 N hydrochloric acid was further added to adjust a pH value to below 3.5, and the piretanide polymorph thus separated out was recovered by filtration and then dried over phosphorus pentoxide under reduced pressure at room temperature for a period of 12 hours to obtain 9.5 g of the desired polymorph.

EXAMPLE 7

Confirmation of Piretanide Polymorph

1) Confirmation of piretanide by HPLC

The crystal obtained as described in Example 6 was analyzed by HPLC in order to confirm that it is piretanide, as set forth below. About 15 mg of the crystal was weighed and dissolved in 0.5 ml of a 0.1 N aqueous solution of sodium hydroxide and then water was added to make up to an exact volume of 10 ml. An aliquot of 2 ml of this solution was taken and made up to an exact volume of 25 ml with methanol, and used this solution as a sample solution. Performed was the test with 15 μl of a sample under the following conditions:

[Operation conditions]

Detector: an ultraviolet absorption photometer (wavelength: 254 nm)

Column: a stainless steel column 4 mm in inside diameter and 30 cm in length, packed with octadecylsilylated silica gel (10 μm in particle diameter) (μBondapak C18)

Mobile phase: a mixture of methanol, water and glacial acetic acid (60:40:0.2)

Consequently, the crystal obtained as described in Example 6 showed peaks at the same retention time as piretanide did.

2) Confirmation of piretanide by TLC

The crystal obtained as described in Example 6 was analyzed by TLC in order to confirm that it is piretanide.

About 10 mg of the crystal was weighed and dissolved in 1 ml of methanol, and used this solution as a sample solution. 10 μl of the test solution was spotted on a thin layer plate and developed with a developing solvent to a distance of about 10 cm and then the thin layer plate was air dried. The plate was irradiated with ultraviolet light (254 nm) and then observed.

[Operation conditions]

Thin layer plate: Silica gel 60F254 precoated plate with a thickness of 0.25 mm (available from E. Merck AG)

Developing solvent: a mixture of isopropanol, benzene and glacial acetic acid (14:6:1), a mixture of chloroform, methyl ethyl ketone and glacial acetic acid (50:50:1), a mixture of isopropanol, methyl ethyl ketone and glacial acetic acid (50:50:1).

Consequently, the crystal obtained as described in Example 6 showed the same $R_f$ value as piretanide did in the three developing solvents as defined above.

EXAMPLE 8

Instrumental Analysis of Piretanide (Differential Thermal Curve, X-ray Powder Diffraction and Infrared Absorption Spectrum)

The piretamine polymorph obtained as described in Example 6 was analyzed with differential thermal curve (Rigaku Denki K.K., Type: 8085E2), X-ray powder diffraction (Mac Science K.K., Type: MXP$^3$) and infra-red absorption spectrum (JEOL Co., Type: JIR5500), using piretanide form A as a control. The results are shown in FIGS. 2, 3, 5, 6, 8, 9.

EXAMPLE 9

Moisture Determination of Piretanide Polymorph

The moisture content of about 10 mg of the piretanide polymorph obtained as described in Example 6 was determined by means of a moisture determination apparatus (Hiranuma Sangyo K.K., Type: AQ 5).

Consequently, the moisture content as determined by the apparatus was about 0.25 mg. On the basis of the molecular weight of piretanide (367.40) and the molecular weight of water (18.0), it has been found that one molecule of water is included per two molecules of piretanide.

EXAMPLE 10

Solubility of Piretanide Polymorph

The piretanide polymorph obtained as described in Example 6 was analyzed for solubility in a buffer at various pH values by means of a dissolution tester, using piretanide form A as a control.

A sufficient amount of the amorphous piretanide to ensure supersaturation was added to 500 ml each of the buffers at various pH values as indicated below, and about 10 ml of a solution was sampled at appropriate intervals and filtered using a 0.45 µm filter. About 5 ml of the initial solution was discarded and the remainder was used as a sample solution and, if required, diluted with the same buffer, if necessary, solubility was determined by absorbance at 275 nm.

[Operation conditions]

Buffer: pH 1 Potassium chloride-hydrochloric acid system pH 3 Sodium chloride-glycine-hydrochloric acid system pH 6.8 JP XII, second fluid Solution temperature: 37° C.

Solvent volume: 500 ml

Rotating speed: 200 rpm

Consequently, the piretanide polymorph showed a solubility of 12.2 mg and 6.7 mg in 100 ml each of the buffers at a pH value of 1 and 3, respectively, and the respective solubility increased by a factor of 1.6 than that of piretanide form A (7.5 mg/100 ml at a pH value of 1 and 4.2 mg/100 ml at a pH value of 3). The piretanide polymorph in a neutral environment showed a solubility of 927.3 mg in 100 ml of a buffer at a pH value of 6.8 and its solubility increased by a factor of 4.8 than that of piretanide form A (193.8 mg/100 mg).

As apparent from the above results, the present piretanide polymorph can show a superior solubility in an aqueous solution in acidic and neutral environments, especially in a neutral envinronment. For instance, the solubility at 37° C. in a buffer at a pH value of 1 of the present piretanide polymorph increased by a factor of 1.6 than that of piretanide forms A and an approximately similar solubility to that of piretanide form B, and it also increased by a factor of 4.8 and 4.7 than those of piretanide forms A and B, respectively at 37° C. in a buffer. at a pH value of 6.8. As gastric juice has a pH value of about 1 and an injection has been usually adjusted to a neutral state, the present piretanide polymorph has a higher bioavailability and can be preferably used for a pharmaceutical preparation for oral administration and an injection.

What is claimed is:

1. An amorphous piretanide having the following characteristics:

(a) exothermic peaks at about 136° C. and about 209° C., (b) an endothermic peak at about 207° C., and (c) a melting peak at about 225° C., in differential thermal curves;

(d) a halo-pattern without diffraction peak (2θ) in X-ray powder diffraction analysis; and (e) characteristic absorptions at around 1700 cm$^{-1}$ and 3200–3500 cm$^{-1}$ in an infra red absorption spectrum.

2. A process for preparing the amorphous piretanide as claimed in claim 1, which comprises dissolving piretanide in an aqueous solution of a base, adjusting a pH value of the solution to a pH range of from not less than 3.87 to not more than 4.37 by an acid and recovering the precipitate thus separated.

3. A piretanide polymorph having the following characteristics:

(a) an endothermic peak at about 132° C., (b) an exothermic peak at about 143° C., and (c) a melting peak at about 224° C., in differential thermal curves;

(d) diffraction peaks (2θ) at 10.5, 12.2, 15.6, 19.1, 19.9, 22.0, 22.8, 25.6 and 30.6° in X-ray powder diffraction analysis; and (e) characteristic absorptions at around 1700 cm$^{-1}$ and 3200–3500 cm$^{-1}$ in an infra-red absorption spectrum.

4. A process for preparing a piretanide polymorph as claimed in claim 3, which comprises dissolving piretanide in an aqueous solution of a base, adjusting a pH value of the solution by an acid to a pH range of less than 3.50 and recovering the precipitate thus separated.

5. A compound as claimed in one of claims 1 or 3 for use as a medicament.

6. A compound as claimed in one of claims 1 or 3 for use as a medicament for the treatment and prevention of edema.

7. A pharmaceutical composition containing an effective amount of a compound as claimed in one of claims 1 or 3 together with a pharmaceutically acceptable carrier.

8. A process for the production of a pharmaceutical composition which comprises bringing a compound as claimed in claims 1 or 3 into a suitable administration form together with a physiologically acceptable excipient and, if appropriate, other additives or auxiliaries.

9. A process for the treatment and prevention of edema comprising administering to a host in need thereof an effective amount of a compound as claimed in claims 1 or 3.

10. A process for the treatment and prevention of edema comprising administering to a host in need thereof a pharmaceutical composition as claimed in claim 7.

* * * * *